United States Patent [19]

Long

[11] 3,935,069

[45] Jan. 27, 1976

[54] ENZYMATIC PROCESS USING IMMOBILIZED MICROBIAL CELLS

[75] Inventor: Margaret Esther Long, Winston-Salem, N.C.

[73] Assignee: R. J. Reynolds Tobacco Company, Winston-Salem, N.C.

[22] Filed: Dec. 23, 1974

[21] Appl. No.: 535,615

[52] U.S. Cl. .................. 195/31 F; 195/116; 195/75
[51] Int. Cl.² .......................................... C12B 1/00
[58] Field of Search ............. 195/31 F, 116, 75, 104

[56] References Cited
UNITED STATES PATENTS 3,821,086  6/1974  Lee et al. ............................ 195/116

*Primary Examiner*—Alvin E. Tanenholtz
*Attorney, Agent, or Firm*—Manford R. Haxton; Herbert J. Bluhm

[57] ABSTRACT

Microbial cells having active enzymes associated therewith are flocculated in the presence of certain metallic compounds to give flocculated cell aggregates exhibiting improved hardness. The cell aggregates are effective as immobilized enzyme materials which are useful in enzymatic processes, particularly those which are of the continuous type.

20 Claims, No Drawings

3,935,069

ENZYMATIC PROCESS USING IMMOBILIZED MICROBIAL CELLS

SUMMARY OF THE INVENTION

Microbial cells having active enzymes associated therewith are flocculated in the presence of certain metallic compounds to give stable cell-containing aggregates that are useful for effecting enzymatic transformation of various substrates which are brought into contact with the aggregates. The metallic compounds which are useful include the oxides, hydroxides, phosphates and sulfates of magnesium, calcium, iron and manganese. Preferred flocculating agents are synthetic anionic or cationic polyelectrolytes.

BACKGROUND OF THE INVENTION

U.S. Pat. No. 3,821,086 discloses a process for effecting enzyme-catalyzed reactions in the presence of flocculated cell aggregates which have associated therewith the desired enzyme activity. Such immobilized cells are sufficiently stable to permit their use in continuous-type processes without appreciable losses in enzyme activity over a period of time. Some flocculated microbial cells, however, undergo a certain degree of compaction, adhesion and fissuring under conditions of continuous use thereby resulting in a gradual decrease in substrate solution flow rates through a bed of the flocculated cells. Even though enzyme activities are retained under the conditions of use, the gradual decrease in flow rates in a continuous process limits the utilization of all available enzyme activity in the immobilized cells. The decrease in flow rates becomes much more pronounced as the viscosity of the substrate solution is increased which, for certain enzymatic processes, results in process limitations that are economically unattractive.

DETAILED DESCRIPTION

The present invention provides a means for improving the stability of flocculated cell aggregates so that the cell aggregate particles show a greater resistance to compaction under conditions of use in an enzymatic process. This improved stability greatly enhances the flow rates of substrate solutions through beds of microbial cells flocculated by the method of this invention thereby increasing the useful lifetimes thereof. The processing of substrate solutions of relatively high viscosity is also made possible by the improvements associated with the presently disclosed invention.

Simply stated, this invention involves the flocculation of microbial cells in the presence of certain metallic compounds which compounds have been found to impart a greater degree of hardness to the resulting cell aggregates thus obtained when compared with flocculated cells obtained by the process of U.S. Pat. No. 3,821,086. The metallic compounds which have been found to be effective for this purpose include the oxides, hydroxides, phosphates and sulfates of magnesium, manganese, calcium and iron. The compounds are added to the fermentation broth or cell suspension just prior to the addition of the flocculants. Recovery of the flocculated cell aggregates containing the added metallic compounds may then be effected by conventional means such as filtration or centrifugation. The recovered cell aggregates are then dried sufficiently to permit milling and sieving thereof. This allows selection and use of a particular particle size for use in the continuous enzymatic process contemplated. Drying of the aggregates may be carried out at any suitable temperature so long as the enzyme activity of interest is not adversely affected.

The effectiveness of the present invention is shown by results obtained in the treatment of microbial cells with magnesium oxide. Fermentation of Arthrobacter NRRL B-3728 was carried out using the procedure described in Example 1 of U.S. Pat. No. 3,821,086. A 19-liter portion of the resulting fermentation broth was treated with 7.6 liters of a 1 percent Primafloc C-7 solution (previously adjusted to pH 5) followed by 7.6 liters of a 1 percent Primafloc A-10 solution (previously adjusted to pH 7). Primafloc C-7 and A-10 are cationic and anionic flocculants, respectively, which were obtained from Rohm and Haas of Philadelphia, Pennsylvania. Following addition of the flocculants to the broth, gentle agitation of the broth was continued for 5 minutes and the resulting flocculated cells were recovered by filtration. The wet flocculated cell aggregates were then extruded and the extrudate was dried at 55° C. in a forced-draft oven for 18 hours. The dried material was ground in a Wiley mill and particles of 16–20 mesh were collected by sieving. These 16–20 mesh particles were assayed for glucose isomerase activity and found to have 62.7 milliunits per gram. A second 19-liter portion of the Arthrobacter fermentation broth was stirred vigorously with 60 grams of magnesium oxide (Magmaster No. 340 obtained from Michigan Chemical Corporation of Chicago, Illinois) until the pH had increased from 5.7 to 8.5. Further processing of this magnesium oxide-treated broth was the same as above. The dried 16–20 mesh particles were found to contain 52.1 milliunits per gram of glucose isomerase activity.

A procedure for making a preliminary evaluation of the effectiveness of a given additive involves the use of an instrument which measures the hardness or resistance to compression of the particles produced. An instrument which has been found to be suitable for this purpose is the Instron Model 1132 Food Testing System obtained from Instron Corporation in Canton, Massachusetts. The particles to be tested are placed between flat surfaces, one of which is movable at a predetermined speed in the direction of the stationary surface. This instrument is capable of measuring the force required to compress the particles to a preset thickness. Using a thickness of 0.0015 inch (i.e., the movable surface penetrates to within 0.0015 inch of the stationary surface), it has been found that good correlation exists between the measured values and the performance of the cell aggregate particles when used in an enzymatic process. In other words the flow rates of substrate solutions through beds of flocculated cells become more resistant to decreases as the measured resistance to compression of the flocculated cell particles increases.

The hardness of flocculated Arthrobacter NRRL B-3728 cells was evaluated by using the Instron Model 1132 system referred to above. The dried 16–20 mesh particles obtained in each case were immersed in water at room temperature and allowed to stand for 4 hours in order to induce any swelling of the particles. The water covering the cell-containing particles was then replaced with an equal volume of a 2 M glucose solution which had been buffered to pH 8.0 and the resulting immersed cells were maintained at 60° C. overnight. Immersion of the particles in 2 M glucose was effected in order to simulate conditions to which the cell aggregate particles would be subjected when used for isomerizing glucose. Measurement of hardness of the particles with the Instron system was done by randomly selecting 10 individual particles from the immersed sample being investigated, removing excess glucose solution from the particles by briefly contacting them with absorbent paper and immediately placing them on the flat measuring surface of the instrument so that the particles were grouped closely together in the central portion of the measuring surface but not touching each other. Using a drive speed of 5 centimeters per minute, a chart speed of 5 centimeters per minute and a force range of 50 kilograms full scale, the magnesium oxide treated cell aggregates required a force of 9.5 kilograms while the control cell aggregate particles required only 3.3 kilograms.

Evaluation of the flocculated Arthrobacter cells was also made under continuous column operating conditions in order to determine flow rates over extended periods of time. For this test 75 grams of the dried 16–20 mesh particles obtained from each of the two flocculations were immersed in water for a period of time to permit any swelling of the particles. The material was then washed with 8 liters of 0.004 M magnesium chloride that contained 0.1 M sodium bicarbonate as a buffer. The washed particles in each case were packed into 1-inch diameter jacketed columns that were heated to 60° C. A 50-percent by weight glucose solution was allowed to flow by gravity through each column andd the flow rates were monitored hourly. The results shown in Table 1 clearly indicate that the flocculated cells containing magnesium oxide exhibit a more gradual decrease in glucose solution flow rates than do the "untreated" cells.

TABLE 1

Comparative Glucose Solution Flow Rates Through Beds of Flocculated *Arthrobacter* Cells

| Bed Composition | Glucose Soln. Flow Rate (liters/hour) Initial | Final | Total Volume of Glucose Soln. (liters) | Total Operating Time (hrs.) |
| --- | --- | --- | --- | --- |
| Cells Flocculated with Primafloc C-7 and A-10, 75 grams of 16–20 Mesh Particles | 21.9 | 6.0 | 349.8 | 44 |
| Cells Flocculated with Primafloc C-7 and A-10 and containing Magnesium Oxide, 75 grams of 16–20 Mesh Particles | 21.0 | 13.8 | 681.75 | 44 |

In addition to magnesium oxide, a number of other compounds have been found to be effective in producing flocculated Arthrobacter cell aggregates with increased hardness as determined by the Instron Model 1132 measuring system. Shown in Table 2 are the results obtained with various additives used in accordance with the present invention. The experimental procedures for obtaining these data were similar to those described above. It will also be noted in Table 2 that certain compounds such as magnesium carbonate, magnesium chloride and calcium carbonate were found to be ineffective when used in accordance with the presently disclosed process.

TABLE 2

Flocculation of *Arthrobacter* NRRL B-3728 Cells in Presence of Various Additives Using Primafloc C-7 and A-10 Flocculating Agents

| Additive (Use Level: 2.5 g./liter of broth) | Hardness of 16–20 Mesh Particles by Instron (kg.) | Glucose Isomerase Activity (mμ/g.) |
| --- | --- | --- |
| Control (No additive) | 3.3 | 62.7 |
| Magnesium oxide, C.P. | 21.5 | 54.4 |
| Magnesium hydroxide | 10.5 | 43.1 |
| Magnesium monohydrogen phosphate | 7.4 | 45.4 |
| Calcium oxide | 7.5 | 37.2 |
| Calcium hydroxide | 8.0 | 35.0 |
| Calcium triphosphate | 4.6 | 54.6 |
| Calcium sulfate | 6.0 | 53.5 |
| Manganese monoxide | 6.7 | 40.4 |
| Ferric oxide | 5.4 | 46.5 |
| Magnesium carbonate | 2.9 | 59.4 |
| Magnesium chloride | 2.2 | 41.3 |
| Calcium carbonate | 2.8 | 49.6 |

The effectiveness of the presently disclosed invention has also been evaluated using another microorganism known to produce glucose isomerase. Streptomyces albus ATCC 21132 was inoculated into a medium (250 milliliters) containing 1% peptone, 0.25% yeast extract, 0.5% meat extract, 0.05% magnesium sulfate heptahydrate, 0.5% sodium chloride, 2% xylose and 0.003 M cobalt chloride. The medium was incubated in a one-liter flask on a rotary shaker at 30° C. for 48 hours and was then used as the inoculum for a 10-liter fermentation. A New Brunswick fermentor was used for the 10-liter fermentation which was allowed to proceed for 48 hours with an aeration rate of 2.5 liters per minute and agitation at 200 r.p.m. Flocculation of the resulting mycelial suspension was carried out using the general procedure described earlier for Arthrobacter NRRL B-3728. Evaluation of the flocculated aggregates was done as before and results are summarized in Table 3.

TABLE 3

Flocculation of *Streptomyces albus* albus ATCC 21132 in Presence of Various Flocculants and Additives

| Flocculant and Use Level | Additive (Use Level: 2.5 g./liter of broth) | Hardness of 16–20 Mesh Particles by Instron (kg.) | Glucose Isomerase Activity (mμ/g.) |
| --- | --- | --- | --- |
| Primafloc C-7 (13.5 g./l. | | | |

TABLE 3-continued

Flocculation of *Streptomyces albus* albus ATCC 21132
in Presence of Various Flocculants and Additives

| Flocculant and Use Level | Additive (Use Level: 2.5 g./liter of broth) | Hardness of 16-20 Mesh Particles by Instron (kg.) | Glucose Isomerase Activity (mμ/g.) |
|---|---|---|---|
| added as a 2.7% aqueous solution) followed by Primafloc A-10 (4.35 g./l. added as a 2.9% aqueous solution) | Control (No Additive) | 22.0 | 12.4 |
| Primafloc C-7 (13.5 g./l. added as a 2.7% aqueous solution) followed by Primafloc A-10 (4.35 g./l. added as a 2.9% aqueous solution) | Magnesium oxide | 40.0 | 5.85 |
| Cat-Floc$^a$ (2.5 ml./l. added without prior dilution) | Control (No Additive) | 6.5 | 12.0 |
| Cat-Floc$^a$ (2.5 ml./l. added without prior dilution) | Magnesium oxide | 34.0 | 1.8 |
| Delfloc 763$^b$ (2.5 ml./l. added without prior dilution) | Control (No Additive) | 3.2 | 10.0 |
| Delfloc 763$^b$ (2.5 ml./l. added without prior dilution) | Calcium hydroxide | 6.5 | 5.9 |

$^a$Cat-Floc is polydiallyldimethyl ammonium chloride, a cationic polyelectrolyte available from the Calgon Corporation in Pittsburgh, Pennsylvania.
$^b$Delfloc 763 is a cationic polyamide-epichlorohydrin type polyelectrolyte available from Hercules Incorporated of Wilmington, Delaware.

The flocculation of a lactase-producing microorganism in the presence of an inorganic additive in accordance with this invention is exemplified by the treatment of a Bacillus coagulans. This organism is described in copending application, U.S. Ser. No. 529,329, filed Dec. 4, 1974. Cultivation of Bacillus coagulans was carried out in a medium containing 1% proteose peptone, 1% yeast extract, 0.8% potassium dihydrogen phosphate and 2% lactose (sterilized separately). The pH of the medium was 6.0 and incubation at 45° C. for 48 hours was effected on a rotary shaker. At the end of the incubation period toluene was added to the broth (0.5% on a volume per volume basis) and the mixture was agitated for 30 minutes. Flocculation and recovery of the resulting flocculated cell aggregates was carried out using the general procedure described above for Arthrobacter NRRL B-3728 except that 4.5 grams per liter of broth of Primafloc C-7 was added as a 1.5% aqueous solution followed by 1.5 grams per liter of broth of Primafloc A-10 was added as a 1% aqueous solution. Evaluation of the flocculated aggregates (16-20 mesh particles) was done in the usual manner except that the particles were immersed in a 2% lactose solution maitained at 60° C. instead of 2 M glucose to give an Instron hardness of 4.6 kg. An assay of the lactase activity associated with these particles revealed 38.5 units of activity per gram (dry weight) using the assay method described by Weetall et al. in Biotechnology and Bioengineering 16, 295 (1974). The flocculation procedure for Bacillus coagulans was then repeated except that magnesium oxide (2.5 grams per liter of broth) was added to the broth just prior to flocculation. The resulting 16–20 mesh particles were found to have an Instron hardness of 6.0 kg. and a lactase activity of 26.5 units.

The selection of a particular additive for use in the present invention will be influenced by several factors including the stability of the enzyme of interest, the optimum pH range for the enzymatic transformation contemplated and the response of the microbial cells to the flocculants in the presence of the additive selected. For example, an alkaline additive such as calcium oxide would not be suitable for use with an enzyme having optimum activity at pH 4. Final selection of an additive is, of course, based on actual performance under the conditions of use so that some experimentation is necessary to determine the optimum formulation. Determination of this optimum formulation is most conveniently carried out by first selecting the flocculating agent or agents to be used and the optimum use levels thereof. The effectiveness of various additives at different concentration levels can then be easily evaluated by routine experimentation.

The amount of the additive required to produce the desired hardness may vary from about 1% to about 12% by weight of the wet cells being flocculated. The preferred use level is from about 2% to about 6% by weight of the wet cells.

It is readily apparent from the above teachings that a large number of variations may be made in the practice of this invention with respect to the microbial cells immobilized, the enzymatic conversion effected and the flocculating agent or agents used. Those modifications and equivalents which fall within the spirit of the invention and scope of the appended claims are to be considered part of the invention.

What is claimed is:

1. A process for effecting an enzyme-catalyzed transformation of a substrate which comprises contacting the substrate, under conditions suitable for effecting said enzyme catalyzed transformation, with an aggregate comprising microbial cells having associated therewith active quantities of said enzyme, a polyelectrolyte flocculating agent and amounts of an oxide, hydroxide, phosphate or sulfate of a metal selected from the group consisting of magnesium, calcium, iron and manganese sufficient to produce increased hardness in the aggregate and recovering the transformed substrate, said aggregate having been dried prior to use in said transformation.

2. A process according to claim 1 in which the enzyme is glucose isomerase and the tranformation is the conversion of glucose to fructose.

3. A process according to claim 2 in which the metal is magnesium.

4. A process according to claim 2 in which the metal is calcium.

5. A process according to claim 2 in which the metal is iron.

6. A process according to claim 2 in which the metal is manganese.

7. A process according to claim 2 in which the cells are obtained from a member of the genus Streptomyces.

8. A process according to claim 2 in which the cells are obtained from a member of the genus Arthrobacter.

9. A process according to claim 1 in which the enzyme is lactase and the transformation is the conversion of lactose to a mixture containing glucose and galactose.

10. A process according to claim 9 in which the cells are obtained from a member of the genus Bacillus.

11. A process for preparing an aggregate of microbial cells capable of effecting an enzyme-catalyzed transformation of a substrate which comprises flocculating microbial cells having associated therewith active quantities of said enzyme with a polyelectrolyte flocculating agent in the presence of an oxide, hydroxide, phosphate or sulfate of a metal selected from the group consisting of magnesium, calcium, iron and manganese in amounts sufficient to produce increased hardness in the aggregate, recovering the flocculated cell aggregates and drying said cell aggregated sufficiently to permit milling and sieving thereof.

12. The process of claim 11 in which the metal is magnesium.

13. The process of claim 11 in which the metal is calcium.

14. The process of claim 11 in which the metal is iron.

15. The process of claim 11 in which the metal is manganese.

16. A process according to claim 12 in which the enzyme is glucose isomerase and the microbial cells are obtained from a member of either Streptomyces or Arthrobacter.

17. A dried enzyme-containing microbial cell aggregate capable of effecting enzymatic transformation of a substrate contacted therewith comprising polyelectrolyte-flocculated microbial cells having active quantities of said enzyme associated therewith, said aggregate containing amounts of an oxide, hydroxide, phosphate or sulfate of a metal selected from the group consisting of magnesium, calcium, iron and manganese sufficient to produce increased hardness in said aggregate.

18. An aggregate according to claim 17 in which the polyelectrolyte is selected from the group consisting of synthetic anionic and cationic polyelectrolytes.

19. An aggregate according to claim 18 in which the enzyme is glucose isomerase, the microbial cells are obtained from a member of the genus Arthrobacter and the metal is magnesium.

20. An aggregate according to claim 18 in which the enzyme is glucose isomerase, the microbial cells are obtained from a member of the genus Streptomyces and the metal is magnesium.

* * * * *